United States Patent
Ueda et al.

(10) Patent No.: US 9,226,926 B2
(45) Date of Patent: Jan. 5, 2016

(54) THERAPEUTIC AGENT FOR LOWER URINARY TRACT DISEASE

(71) Applicant: N.M.A. Co., Ltd., Nara (JP)

(72) Inventors: Tomohiro Ueda, Kyoto (JP); Yasuhito Funahashi, Aichi (JP)

(73) Assignee: N.M.A. CO., LTD., Nara (JP)

( * ) Notice: Subject to any disclaimer, the term of this patent is extended or adjusted under 35 U.S.C. 154(b) by 0 days.

(21) Appl. No.: 14/140,736

(22) Filed: Dec. 26, 2013

(65) Prior Publication Data

US 2015/0099778 A1 Apr. 9, 2015

(30) Foreign Application Priority Data

Oct. 3, 2013 (JP) .................................. 2013-208646

(51) Int. Cl.
*A01N 43/42* (2006.01)
*A61K 31/47* (2006.01)
*A61K 31/4704* (2006.01)

(52) U.S. Cl.
CPC .................................. *A61K 31/4704* (2013.01)

(58) Field of Classification Search
None
See application file for complete search history.

(56) References Cited

U.S. PATENT DOCUMENTS

| 2003/0170286 A1* | 9/2003 | Ashton et al. | 424/423 |
| 2007/0202151 A1* | 8/2007 | Lee et al. | 424/426 |
| 2008/0004596 A1* | 1/2008 | Yun et al. | 604/508 |

OTHER PUBLICATIONS

Pentyala et al., "Current perspectives on pyospermia: a review," Asian J Androl 2007; 9(5):593-600.*
STN CAS RN: 169809-59-0 (entered Nov. 8, 1995).*
Serajuddin, "Salt formation to improve drug solubility," Advanced Drug Delivery Reviews 59 (2007) 603-616.*

* cited by examiner

*Primary Examiner* — Craig Ricci
*Assistant Examiner* — Jared D Barsky
(74) *Attorney, Agent, or Firm* — Price Heneveld LLP

(57) ABSTRACT

A method of treating a condition chosen from the group consisting of interstitial cystitis, cystitis, chronic nonbacterial prostatitis, chronic cystitis, prostatic hyperplasia, prostatitis, prostatism, bladder neck contracture, bladder inflammation, and overactive bladder by administering an amount of rebamipide or a pharmaceutically acceptable salt thereof to a human.

13 Claims, 4 Drawing Sheets

THERAPEUTIC AGENT FOR LOWER URINARY TRACT DISEASE

CROSS-REFERENCE TO RELATED APPLICATION

This application claims priority to Japanese Patent Application No. 2013/208646 entitled THERAPEUTIC AGENT FOR LOWER URINARY TRACT DISEASE filed on Oct. 3, 2013, the entire disclosure of which is hereby incorporated by reference.

BACKGROUND OF THE INVENTION

The present invention relates to a therapeutic agent for lower urinary tract disease, especially for interstitial cystitis.

Lower urinary tract disorder is a general term for dysfunction of lower urinary tract. Lower urinary tract symptoms, which are those resulting from lower urinary tract disorder, are mainly classified into three categories: urine storage symptoms (pollakiuria, feeling of urinary urgency and the like), urinary symptoms (decreased urinary spontaneity, splitting of urinary stream and the like), and post urinary symptoms (feeling of residual urine, dribbling after urination and the like). Further, lower urinary tract symptoms include lower urinary tract pains such as urodynia, cystalgia and urethral pain; overactive detrusor muscle; dysuria and the like. Hematuria may also be observed for lower urinary tract disorder. Diseases responsible for lower urinary tract disorder (lower urinary tract diseases) include prostatic hyperplasia, prostatitis, prostatism, bladder neck sclerosis, overactive bladder, chronic cystitis, interstitial cystitis, bladder pain syndrome and the like.

Among these, in particular, interstitial cystitis is intractable disease which is manifested by symptoms such as pollakiuria, uresiesthesia, feeling of urinary urgency, bladder discomfort and cystalgia, but shows neither urinary tract infection nor other clear pathological conditions. Although more women are affected, this disorder is developed regardless of sex and age. The number of patients is estimated to be 250,000 or more in Japan and one million or more in U.S. However, international consensus has not yet been reached with regard to the definition and diagnostic criteria of interstitial cystitis. Interstitial cystitis may also be called bladder pain syndrome (BPS) or hypersensitive bladder syndrome (HBS).

Further, chronic nonbacterial prostatitis (non-bacterial chronic prostatitis), which represents a condition in which chronic inflammation in prostate gland continues, accounts for 90% of chronic prostatitis. In many cases, it occurs in conjunction with interstitial cystitis, causing dull pain and discomfort in the scrotal position and the like or urinary symptoms such as pollakiuria, painful urination and feeling of residual urine. It is similar to interstitial cystitis in it shows symptoms such as pain before and after ejaculation and the like. The cases of chronic nonbacterial prostatitis are limited to males, but the number of the patients is said to be 700,000 to 1 million, which is greater than that of interstitial cystitis.

Possible causes of interstitial cystitis and non-bacterial chronic cystitis include activation of mast cells, abnormal glycosaminoglycan layer, urothelial cell growth inhibition, autoimmunity, neurogenic inflammation, nitric oxide metabolism, toxic substance, hypoxia and the like. Nonetheless a clear cause has not yet been known.

Although interstitial cystitis is often accompanied by non-specific chronic inflammation in bladder, anti-inflammatory agents such as steroid do not show efficacy in the disease and an animal model of the disease. This suggests that inflammation itself has not caused the symptoms such as pollakiuria in the disease. Yet unknown causes of these diseases make it difficult to develop therapeutic agents. Agents currently used for treatment include antihistamine, antidepressant, cimetidine, antibiotics, steroid, pentosan polysulfide and the like, all of which are for symptomatic treatment and do not serve as effective treatment methods. Only suplatast tosilate has been a potentially etiotropic substance, but its efficacy remains unsatisfactory.

As described above, unlike other cystitis, use of antibiotics and antimicrobial agents do not show efficacy for interstitial cystitis. Despite severe pain associated with interstitial cystitis, there is no useful therapeutic agent at present, and in some cases, there is no choice but to remove the bladder eventually. Therefore, many patients are left to live a significantly difficult day-to-day life because of these symptoms.

For information, one of the present inventors, Tomohiro UEDA has been recognizing that interstitial cystitis in itself is also difficult to be diagnosed, and involves severe pain. Accordingly, in order to ease burden of patients suffering from interstitial cystitis, he has invented: a catheter for diagnosing interstitial cystitis connectable to an electric current perception threshold testing system (CPT system) when in use, which allows intravesical diagnose upon insertion into urethra (U.S. Pat. No. 7,338,480); a method for diagnosing interstitial cystitis (U.S. Pat. No. 8,010,185); a device of protecting urethra for use in diagnosing interstitial cystitis (Japanese Patent No. 5175988) and the like. However, as described above, a useful therapeutic agent is not available.

SUMMARY OF THE INVENTION

An aspect of the present disclosure includes a method of treating a condition chosen from the group consisting of interstitial cystitis, cystitis, chronic nonbacterial prostatitis, chronic cystitis, prostatic hyperplasia, prostatitis, prostatism, bladder neck contracture, bladder inflammation, and overactive bladder by administering an amount of rebamipide or a pharmaceutically acceptable salt thereof to a human.

Yet another aspect of the present disclosure is a method of treating a condition of a patient chosen from the group consisting of interstitial cystitis, cystitis, chronic nonbacterial prostatitis, chronic cystitis, prostatic hyperplasia, prostatitis, prostatism, bladder neck contracture, bladder inflammation, and overactive bladder by administering a therapeutically effective amount of rebamipide or a pharmaceutically acceptable salt thereof to the patient in need thereof.

Another aspect of the present disclosure is a kit that includes: (1) a pharmaceutical composition comprising rebamipide or a pharmaceutically acceptable salt thereof in an amount effective to treat a condition chosen from the group consisting of interstitial cystitis, cystitis, chronic nonbacterial prostatitis, chronic cystitis, prostatic hyperplasia, prostatitis, prostatism, bladder neck contracture, bladder inflammation, and overactive bladder in a human when administered to a human and wherein the pharmaceutical composition is configured to be administered to a human using a catheter; and (2) a catheter configured to administer the pharmaceutical composition into a urinary tract of the human. The kit may also contain a syringe configured to engage the catheter and deliver the pharmaceutical composition through the catheter into the urinary tract of the human.

Accordingly, an object of the present invention is to provide a new therapeutic agent and a new treatment method which are effective for lower urinary tract disease, especially for interstitial cystitis.

In order to solve the above problem, a therapeutic agent for lower urinary tract disease according to the present invention comprises rebamipide as an active ingredient.

Further, the active ingredient may be 2-(4-chlorbenzoylamino)-3-(2-quinolone-4-yl)propionic acid or a salt thereof.

Furthermore, a formulation according to the present invention contains 2-(4-chlorbenzoylamino)-3-(2-quinolone 4-yl) propionic acid or a salt thereof and a pharmaceutical carrier for bladder. Preferably, the formulation may be in a liquid form or a suspension form, or may be an injectable.

Further, the present invention encompasses use of rebamipide or a pharmaceutically acceptable salt thereof for manufacture of a therapeutic agent for interstitial cystitis; rebamipide or a pharmaceutically acceptable salt thereof for use in treating interstitial cystitis; and a method of treating interstitial cystitis comprising administrating a therapeutically effective amount of rebamipide or a pharmaceutically acceptable salt thereof to a patient suffering from interstitial cystitis. Furthermore, the present invention also encompasses a therapeutic agent and a treatment method useful for lower urinary tract disease in addition to interstitial cystitis.

That is, after intensive studies, the present inventors found that rebamipide, which is currently used for gastric ulcer or as eye drops, is effective for treatment of lower urinary tract disease, especially for interstitial cystitis, and that also effective for treatment of other cystitis and prostatitis. Then the present inventors completed the present invention.

Rebamipide is a carbostyril derivative represented by the following formula (I), Formula I

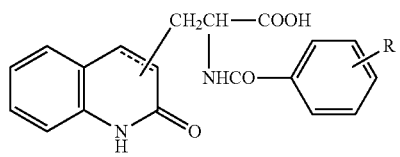

(I)

wherein R represents a halogen atom; the carbostyril backbone is substituted at position 3 or 4; and a bond between positions 3 and 4 on the carbostyril backbone represents a single or double bond, and is generally termed as 2-(4-chlorbenzoylamino)-3-(2-quinolone-4-yl)propionic acid. Rebamipide is already commercially available, and used in a form of tablet useful for gastric ulcer and acute gastritis, and also used as eye drops useful for ameliorating subjective symptom of dry eye (WO97/13515 and the like).

For the pharmaceutically acceptable salt of rebamipide, a variety of physiologically or pharmaceutically acceptable salts can be used. They include, for example, salts formed with sodium hydroxide, potassium hydroxide, trometamol, monoethanolamine, diethanolamine, triethanolamine, diisopropanolamine, meglumine and the like.

The therapeutic agent according to the present invention contains rebamipide or a salt thereof as an active ingredient, and is prepared in a form of a general pharmaceutical formulation. For example, the formulation is prepared using commonly used diluent or excipient such as filler, expander, binder, wetting agent, disintegrating agent, surfactant and lubricant. Forms of the pharmaceutical formulation include various known forms such as solution, injectable, suspension, tablet, powder, emulsion, granule, capsule and aerosol, but solution, suspension or injectable is desirable since direct injection into bladder is preferred for treatment of lower urinary tract disease, especially interstitial cystitis.

When formulated as injectable, the formulation is prepared as solution, emulsion or suspension. It is sterilized as in the normal injectable to achieve asepsis, and is preferably isotonic to blood. For diluents used for the forms of solution, emulsion and suspension, those generally known and commonly used can be used. For example, water, ethoxylated isostearyl alcohol, ethyl alcohol, propylene glycol and polyoxyethylene sorbitan fatty acid esters can be used. In addition, an isosmotic solution may be prepared using sodium chloride, glucose, glycerin. In addition, a solubilizing agent, a buffer agent, a soothing agent, a preserving agent, a coloring agent and the like can be used if desired.

Solubilizing agents include, for example, carboxymethylcellulose sodium, polyoxyethylene lauryl ether, polyoxyethylene glycol ethers, polyethylene glycol higher fatty acid esters, polyoxyethylene sorbitan monolaurate, polyoxyethylene fatty acid ester and the like. Buffer agents include, for example, sodium phosphate, disodium hydrogenphosphate, potassium hydrogenphosphate, sodium borate, citric acid, sodium citrate, tartaric acid, sodium tartrate, acetic acid, sodium acetate, epsilon aminocaproic acid, sodium glutamate and the like. Antioxidants include, for example, sodium sulfite, sodium pyrosulfite, sodium bisulfite, sodium thiosulfite, ascorbic acid and the like. Antiseptic agents include, for example, chlorobutanol, benzalkonium chloride, benzethonium chloride, phenylmercuric salt, thimerosal, phenethyl alcohol, methylparaben, propylparaben and the like. Isotonizing agents include, for example, sodium chloride, glucose, D-mannitol, glycerin and the like. Solubilizers include N-methyl glutamine and the like. pH adjusting agents include, for example, sodium hydroxide, hydrochloric acid and the like.

The present invention can use a commercially available form of suspension (eye drops). Suspension (eye drops) can be manufactured by mixing rebamipide with a base material such as sterile distilled water, and then performing sterilization. Further, known or conventional solubilizing agent, buffer agent, antiseptic agent, isotonizing agent, pH adjuster and the like may be formulated as needed. A specific commercially available form contains 20 mg/ml rebamipide as an active ingredient. Further, it contains polyvinyl alcohol (partially saponified substance), sodium citrate hydrate, sodium chloride [isotonizing agent], potassium chloride [isotonizing agent], hydrochloric acid [pH adjuster], sodium hydroxide [pH adjuster] and purified water as additives, and has a pH of 5.5 to 6.5 and an osmotic pressure ratio of 0.9 to 1.1 (a ratio to physiological saline). An appropriate amount of the above suspension (for example, about 20 ml) can be injected into patient's bladder through a syringe, a catheter and the like, depending on the conditions of the bladder. However, the form, concentration, dose frequency and dosage are not limited to those described above as long as they are effective for treatment of interstitial cystitis. They can be appropriately selected depending on the conditions of patient's bladder and the like.

These and other features, advantages, and objects of the present invention will be further understood and appreciated by those skilled in the art by reference to the following specification, claims, and appended drawings.

DETAILED DESCRIPTION

All of the patients in Examples below have been endoscopically diagnosed as interstitial cystitis, and have not shown a response to the bladder hydrodistension procedure which is the only approved treatment in Japan, but are still suffering from pain. More specifically, they are patients who are suffering prolonged pain even on the injection of 4% xylocaine alone or 20 ml of 4% xylocaine+100 ml amikacin+300 mg Saxizon.

Treatment contents involve an injection of about 8 cc Mucosta (registered trademark) eye drops in a syringe into the bladder through a catheter using 28 packages of the eye drops (for 1 hour or more).

Example 1

Eighty years old (male), first visit on Apr. 9, 2012.

The chief complaint was cystalgia on urine storage and urethral pain in conjunction with non-bacterial chronic prostatitis.

He received the bladder hydrodistension procedure at certain municipal hospital, but complained strong recurrent cystalgia. Accordingly the above treatment was performed on Jul. 24 and 31 in 2013.

Figure 1:
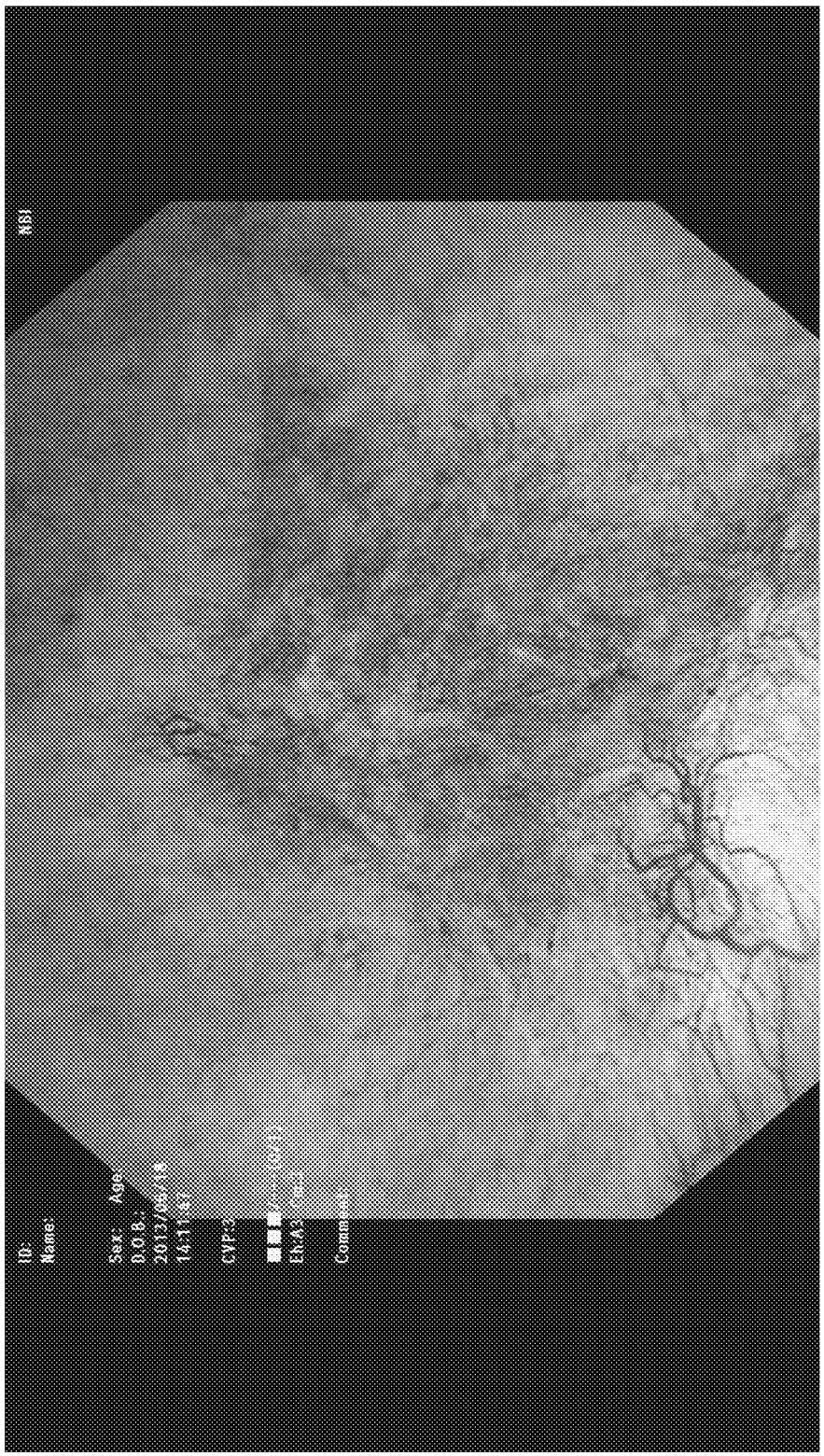
FIG. 1 is an endoscopic photograph of the bladder of the patient described in Example 1 before treatment.
Figure 2:
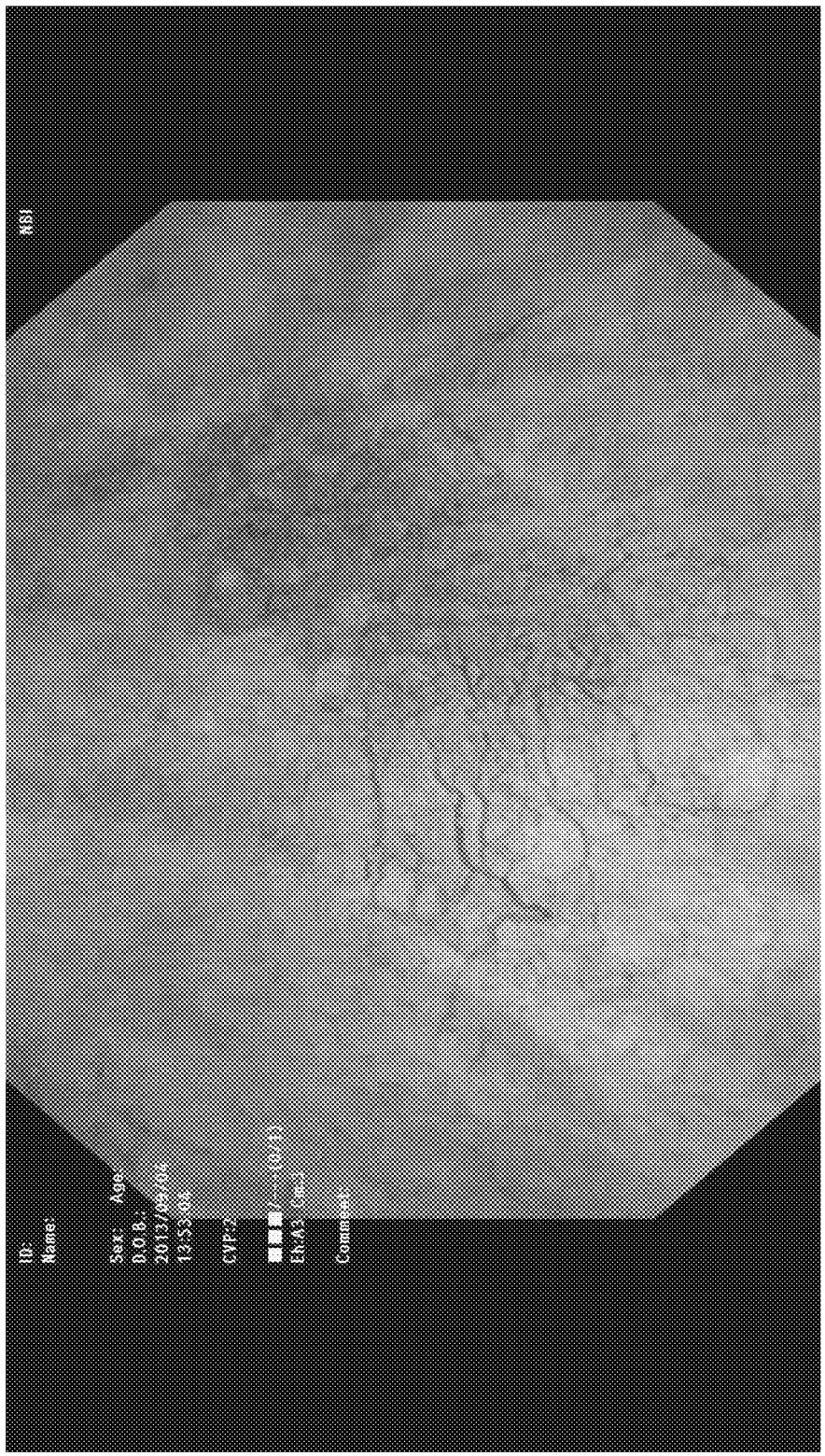
FIG. 2 is an endoscopic photograph of the bladder of the patient described in Example 1 after treatment.

As a result, pain has disappeared to date. Bladder ulcer also has been ameliorated as easily observed by visual inspection on endoscope photographs (FIGS. 1 and 2). No adverse effect was observed.

Example 2

Seventy nine years old (female), first visit on Apr. 2, 2012.

The treatment as described above was performed 6 times, i.e., on Jul. 26, 29, 30 and 31, and Aug. 2 and 3 in 2013.

Figure 3:
FIG. 3 is an endoscopic photograph of the bladder of the patient described in Example 2 before treatment.
Figure 4:
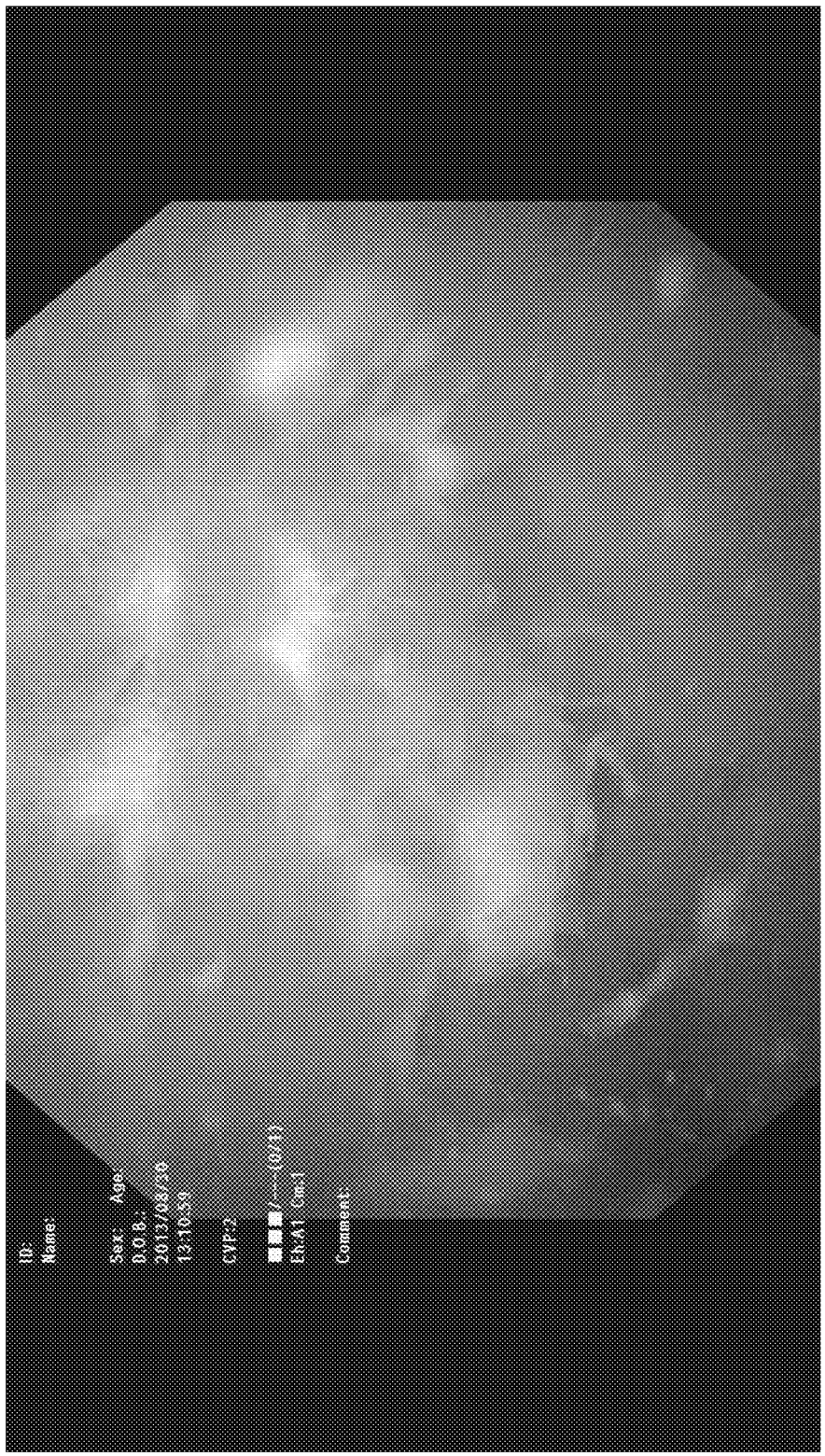
FIG. 4 is an endoscopic photograph of the bladder of the patient described in Example 2 after treatment.

As a result, pain has disappeared to date. Bladder ulcer also has been ameliorated as easily observed by visual inspection on endoscope photographs (FIGS. 3 and 4). No adverse effect was observed.

Example 3

Seventy-four years old (male), first visit on Jun. 11, 2012.

Non-bacterial chronic prostatitis was accompanied.

The treatment as described above was performed on Jul. 29, 2013.

As a result, pain has disappeared to date. No adverse effect was observed.

As described above, the treatment described above all clearly showed efficacy for interstitial cystitis which was considered as intractable disease until that time, and for which there was no effective treatment method. Furthermore, therapeutic effects were also observed for non-bacterial chronic prostatitis that occurred in combination. Note that diagnosis and bladder injections can be performed by using the foregoing invention which the present inventors have previously invented. Therefore, it was possible to perform diagnosis and treatment without causing stress to a patient. In addition, before treatment, treatment contents were explained to the patients, and written consent was also obtained.

In addition, experiments were performed for studying effects of the present invention on cystitis using a rat model of chronic cystitis.

Method

To 12-week old male SD rats, cyclophosphamide (150 mg/kg) was intraperitoneally administered under isoflurane anesthetization. Immediately after that, rebamipide (1 mM or 10 mM, 300 μL) or vehicle was injected into the bladder, and the rats were held in the supine position for 1 hour.

(1) After two days, conscious cystometrography was performed (the saline perfusion flow rate: 0.04 ml/min) was performed.

(2) After two days, the bladder was removed, and H&E stained to score the degree of inflammation (3) TNFα, IL-6 and IL-1β which are inflammatory cytokines in bladder tissue were measured by RT-PCR, and an inflammation marker, MPO, was measured by ELISA.

Results (1) In the cystometry studies, a reduced urination interval was observed in the CYP group (10.7±0.7 min) as compared with the control (22.4±2.3 min) while a prolonged urination interval was observed dose-dependently in the rebamipide group (the 1 mM group; 14.4±2.1 min and the 10 mM group: 21.1±2.5 min).

(2) Submucosal edema and invasive inflammatory cells were significantly higher in the CYP group, and significantly reduced in the rebamipide group.

(3) The levels of TNFα, IL-6, IL-1β and MPO in the bladder tissue were significantly higher in the CYP group, and their increase was suppressed in the rebamipide group.

Bladder inflammation was suppressed by injecting rebamipide into the bladder, and a prolonged urination interval was observed.

As described above, the present invention is effective for not only interstitial cystitis but other cystitis and chronic nonbacterial prostatitis, and also effective for lower urinary tract diseases including chronic cystitis, prostatic hyperplasia, chronic nonbacterial prostatitis, prostatitis, prostatism, bladder neck contracture and overactive bladder. Therefore, the present invention provides a new therapeutic agent and a new treatment method for these diseases.

The invention claimed is:

1. A method of treating bladder ulcer in a subject with a non-bacterial lower urinary tract disease selected from the group consisting of interstitial cystitis and chronic non-bacterial prostatitis comprising injecting a therapeutically effective amount of a liquid form of rebamipide or a pharmaceutically acceptable salt thereof directly into the bladder of a subject in need thereof.

2. The method of claim 1, wherein the step of injecting a therapeutically effective amount of a liquid form of rebamipide comprises administering a therapeutically effective amount of a pharmaceutical composition comprising rebamipide to the human.

3. The method of claim 2, wherein the liquid form of the pharmaceutical composition is selected from the group consisting of a solution, a suspension, an emulsion, or a combination thereof.

4. The method of claim 3, wherein the pharmaceutical composition is a solution, suspension or an injectable composition and the rebamipide is in the form of a pharmaceutically acceptable salt formed with sodium hydroxide, potassium hydroxide, trometamol, monoethanolamine, diethanolamine, triethanolamine, diisopropanolamine, or meglumine.

5. The method of claim 4, wherein the pharmaceutical composition further includes at least one excipient chosen from the group consisting of a filler, an expander, a binder, a wetting agent, a disintegrating agent, a surfactant and a lubricant.

6. The method of claim 5, wherein the pharmaceutical composition further comprises a solubilizing agent.

7. The method of claim 6, wherein the solubilizing agent comprises a solubilizing agent chosen from the group consisting of carboxymethylcellulose sodium, polyoxyethylene lauryl ether, polyoxyethylene glycol ethers, polyethylene glycol higher fatty acid esters, polyoxyethylene sorbitan monolaurate, polyoxyethylene fatty acid ester.

8. The method of claim 2, wherein the pharmaceutical composition further comprises a solubilizing agent chosen from the group consisting of carboxymethylcellulose sodium, polyoxyethylene lauryl ether, polyoxyethylene glycol ethers, polyethylene glycol higher fatty acid esters, polyoxyethylene sorbitan monolaurate, polyoxyethylene fatty acid ester.

9. The method of claim 8, wherein the pharmaceutical composition further comprises an antioxidant.

10. The method of claim 9, wherein the antioxidant is an antioxidant chosen from the group consisting of sodium sulfite, sodium pyrosulfite, sodium bisulfite, sodium thiosulfite, and ascorbic acid.

11. The method of claim 9, wherein the pharmaceutical composition further comprises an antiseptic agent, an isotonizing agent, a solubilizer and a pH adjusting agent.

12. The method of claim 11, wherein the step of administering the therapeutically effective amount of a pharmaceutical composition comprising rebamipide to the human comprises using a syringe and a catheter to deliver the pharmaceutical composition to the bladder of a human.

13. The method of claim 12, wherein the pharmaceutical composition is in the form of a suspension and the pharmaceutical composition is administered to the human for over one hour.

* * * * *